(12) United States Patent
Prater et al.

(10) Patent No.: US 8,242,448 B2
(45) Date of Patent: Aug. 14, 2012

(54) DYNAMIC POWER CONTROL, BEAM ALIGNMENT AND FOCUS FOR NANOSCALE SPECTROSCOPY

(75) Inventors: Craig Prater, Santa Barbara, CA (US);
Michael Lo, Santa Barbara, CA (US);
Doug Gotthard, Carpinteria, CA (US);
Anthony Kurtz, Ventura, CA (US);
Kevin Kjoller, Santa Barbara, CA (US)

(73) Assignee: Anasys Instruments Corporation, Santa Barbara, CA (US)

( * ) Notice: Subject to any disclaimer, the term of this patent is extended or adjusted under 35 U.S.C. 154(b) by 93 days.

(21) Appl. No.: 12/927,248

(22) Filed: Nov. 9, 2010

(65) Prior Publication Data
US 2011/0205527 A1 Aug. 25, 2011

Related U.S. Application Data

(63) Continuation-in-part of application No. 12/660,266, filed on Feb. 23, 2010.

(51) Int. Cl.
*G01J 5/00* (2006.01)
(52) U.S. Cl. .................................................. 250/338.1
(58) Field of Classification Search .......... 250/330–335, 250/336.1–336.2, 338.1–338.5, 339.01–339.15, 250/340, 341.1–341.8; 73/105
See application file for complete search history.

(56) References Cited

U.S. PATENT DOCUMENTS
2009/0249521 A1* 10/2009 Dazzi et al. .................... 850/33

OTHER PUBLICATIONS

J. A. Dvorak, "The application of atomic force microscopy to the study of living vertebrate cells in culture," 2003, Methods, vol. 29, pp. 86-96.*
Kjoller et al., "High-sensitivity nanometer-scale infrared spectroscopy using a contact mode microcantilever with an internal resonator paddle," 2010, Nanotechology, vol. 21, pp. 1-6.*

* cited by examiner

*Primary Examiner* — Kiho Kim
(74) *Attorney, Agent, or Firm* — Mark Rodgers (57) ABSTRACT

Dynamic IR radiation power control, beam steering and focus adjustment for use in a nanoscale IR spectroscopy system based on an Atomic Force Microscope. During illumination with a beam from an IR source, an AFM probe tip interaction with a sample due to local IR sample absorption is monitored. The power of the illumination at the sample is dynamically decreased to minimize sample overheating in locations/wavelengths where absorption is high and increased in locations/wavelengths where absorption is low to maintain signal to noise. Beam alignment and focus optimization as a function of wavelength are automatically performed.

23 Claims, 8 Drawing Sheets

DYNAMIC POWER CONTROL, BEAM ALIGNMENT AND FOCUS FOR NANOSCALE SPECTROSCOPY

RELATED APPLICATIONS

This application is a Continuation-in-Part of U.S. application Ser. No. 12/660,266 filed Feb. 23, 2010

FEDERALLY SPONSORED RESEARCH

This work was supported in part by NIST-ATP 70NANB7H7025 and NSF-SBIR 0750512 The government retains certain rights.

SEQUENCE LISTING

Not Applicable

BACKGROUND OF THE INVENTION

This invention is related to highly localized Infrared (IR) spectra on a sample surface utilizing an Atomic Force Microscope (AFM) and a variable wavelength pulsed IR source, and specifically to dynamic IR power control for maximizing dynamic range while minimizing sample damage.

IR spectroscopy is a useful tool in many analytical fields such as polymer science and biology. Conventional IR spectroscopy and microscopy, however, have resolution on the scale of many microns, limited by optical diffraction. It would be particularly useful to perform IR spectroscopy on a highly localized scale, on the order of biological organelles or smaller, at various points on a sample surface. Such a capability would provide information about the composition of the sample, such as location of different materials or molecular structures. Conventional infrared spectroscopy is a widely used technique to measure the characteristics of material. In many cases the unique signatures of IR spectra can be used to identify unknown material. Conventional IR spectroscopy is performed on bulk samples which gives compositional information but not structural information. Infrared Microscopy allows collection of IR spectra with resolution on the scale of many microns resolution. Near-field scanning optical microscopy (NSOM) has been applied to some degree in infrared spectroscopy and imaging. Recently, a technique has been developed based on use of an AFM in a unique fashion to produce such localized spectra. This work was described in a publication entitled "Local Infrared Microspectroscopy with Sub-wavelength Spatial Resolution with an Atomic Force Microscope Tip Used as a Photo-thermal Sensor" Optics Letters, Vo. 30, No. 18, Sep. 5, 2005. This technique is also described in detail in co-pending applications U.S. Ser. Nos. 11/803,421 and 12/315,859, commonly owned by the assignee of this invention, and whose contents are incorporated by reference. Those skilled in the art will comprehend the details of the technique in the publication and patent applications but the technique will be described briefly herein for clarity. The general technique is also referred to as Photo-Thermal Induced Resonance, or PTIR.

Figure 1:
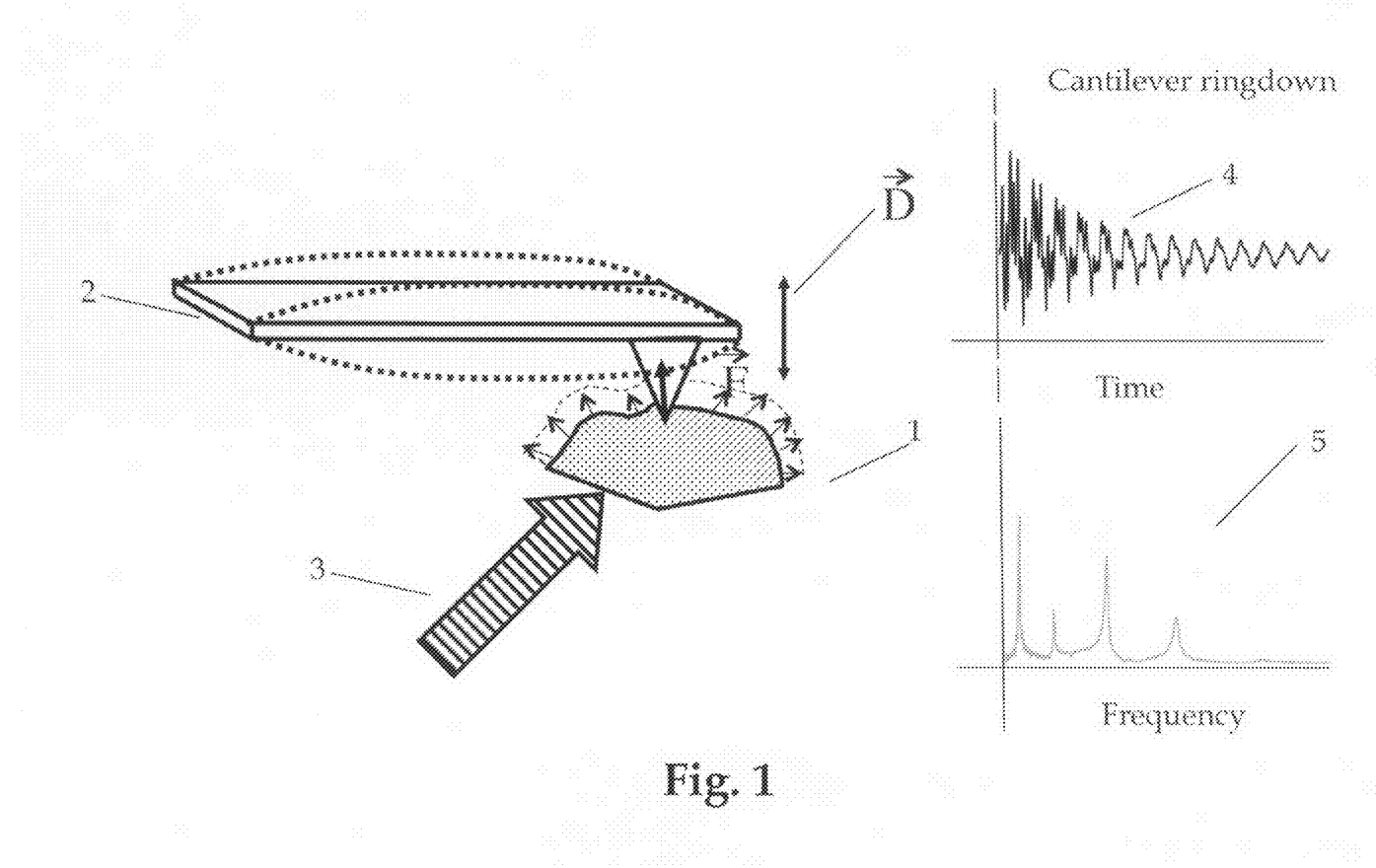
FIG. 1 is a simplified illustration of the PTIR technique

Referring to FIG. 1, the PTIR technique basically uses an Atomic Force Microscope (AFM). A typical AFM cantilever probe 2 is brought in interaction with a region of a sample 1. A beam from pulsed IR radiation source 3 is directed to the sample 1. When a brief, intense radiation pulse illuminates the sample 1, it causes a rapid sample expansion due to thermal shock, stimulating a resonant oscillation 4 of the cantilever probe 2, which is measurable by the AFM's probe deflection detection system. The amplitude of the thermal shock depends on the degree of IR absorption, which will depend on the material characteristics of the sample in the area immediately under the probe tip. The degree of absorption will also depend on the wavelength of the IR radiation. Thus varying the wavelength of the source and repeating the deflection measurement across a range of wavelengths yields an absorption spectrum 5 for a highly localized region of a sample. The measurement may be repeated at a plurality of points on the sample surface, to create an absorption spectra map, enabling characterization and identification of sample material composition at a previously unattainable resolution. Related techniques detect the local temperature change in the sample via a temperature sensing AFM probes, as described by Hammiche and others in the scientific literature.

It has become apparent during applications testing of a commercial nanoscale IR spectroscopy platform there is a challenge between optimizing the signal to noise ratio and the risk of sample damage. The issue is related to the dynamic range of the measurement technique. If the amount of IR energy absorbed is small in some areas of the sample at particular wavelengths, it creates a signal that is below the limit of detection. To increase the signal to noise ratio, the IR laser power can be turned up to increase the amount of absorbed radiation. But if the absorbed IR energy is too high, it causes substantial heating of the sample in other areas and/or wavelengths which can lead to melting, burning and/or chemical changes in the sample. Even at temperatures below a thermal damage threshold, the sample may soften to the point that the pressure of an AFM tip can cause local plastic deformation, altering the topography of the sample. It is desirable to avoid any or all of these potential types of sample damage.

Figure 2:
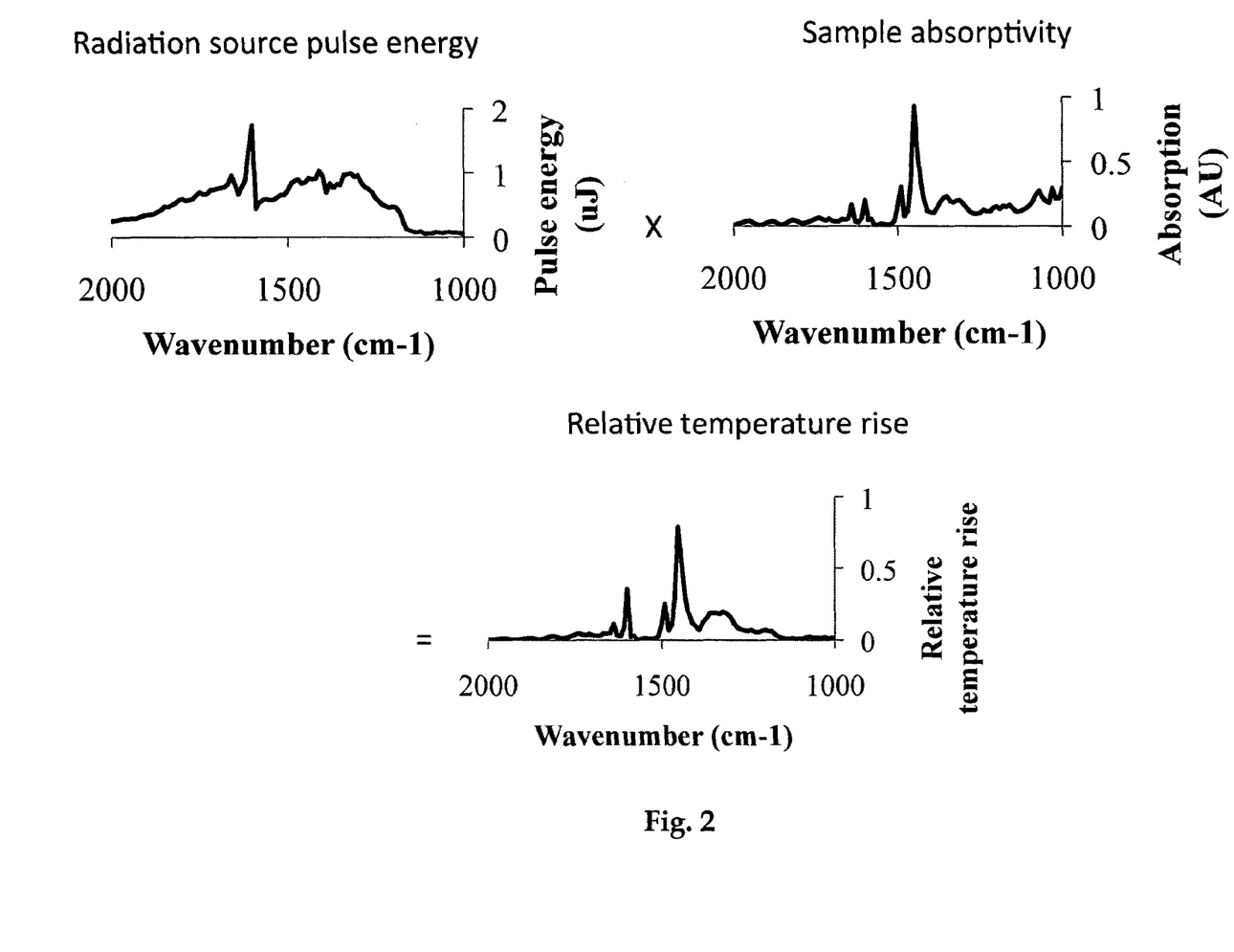
FIG. 2 is an illustration of the source pulse energy, sample absorptivity and temperature rise in a PTIR measurement

The temperature rise in the sample is a function of both the laser power at a given wavelength and the sample absorption at that wavelength, as illustrated in FIG. 2. A suitable radiation source using an optical parametric oscillator (OPO) laser has power variations of almost 20× over the range of 1000-2000 $cm^{-1}$. In addition to this, sample absorption peaks can vary by orders of magnitude. In recently obtained spectra, the ratio between the largest and smallest peak heights can be 20×. So even over the range of 1000-2000 $cm^{-1}$ the sample temperature change could vary by 20×20=400× over peaks of interest. If the laser power is turned up large enough to resolve the smallest peaks, the sample can easily be damaged at the higher peaks. (Note that the x-axes in FIG. 2 are labeled in "wavenumbers (cm−1)" a convention used in spectroscopy. The wavelength in microns is given by 10,000/wavenumber. In this application we use the terms wavenumber and wavelength interchangeably, i.e. measuring a property as a function of wavelength provides equivalent information as measuring a property as a function of wavenumber.)

A typical approach used in the PTIR technique is to use a lens to focus the infrared laser beam onto a region of the sample under the cantilever probe tip. It has also become apparent in testing by the inventors that it can be quite a challenge to determine the optimal alignment of an infrared laser beam and that this alignment process can require tedious experimentation or trial and error to find the best alignment. There are a number of reasons for this. First, the infrared laser beam is invisible to the eye and also to many video cameras. While IR cameras are available they are quite expensive. A common solution is to employ a visible guide beam that is collinear with the infrared beam. This is an imperfect solution, however, especially when the beams pass through refractive optics. The index of refraction of most optical materials has a significant dependence on wavelength. And so going from the visible guide beam to an infrared source, especially a widely tunable infrared source can create significant changes in the amount of refraction caused by a lens or other optical element. This change in refraction can lead to differences in the position of the focus spot created by a lens, particularly when using a monochromatic visible beam as an alignment reference for a broadly tunable infrared source. The differences in position can also be in three axes, one along the beam axis (focus depth) and two lateral axes perpendicular to the beam axis. While these shifts can be minimized by aligning the incident laser beam perpendicular to optical surfaces, in practice it can be difficult to achieve such alignment over a wavelength range, especially when multiple refractive elements are used and/or when one or more of the refractive elements are replaceable by the user (e.g., a sample substrate). However, despite these issues, it can be advantageous to utilize a visible alignment source as a mechanism for rough alignment. Further, tunable infrared sources may have a significant variation in exit beam angle themselves as a function of wavelength and these variations can also translate directly into lateral shifts in the focus position. Uncontrolled shifts in the focus and/or lateral position of the beam can cause loss of signal-to-noise, improper measurements of relative heights of absorption peaks, and/or discontinuities in spectra as the IR source is switched from one stage to another (for example switching from the signal to the idler in an OPO radiation source). This can also be a significant issue since the IR beam may be focused to a diffraction limited spot on the scale of a few to a few 10's of microns. Very small angular shifts could otherwise move the point of this focused spot entirely away from the point of probe-sample interaction. For example, using a 25 mm focal length lens, a 1 mrad shift in the beam position with wavelength can lead to a 25 µm shift in the focused spot position. It is possible to defocus the laser beam to create a larger spot, but-this can compromise the signal-to-noise ratio, especially for weak absorptions and/or wavelengths where the laser source has limited power. This has led to the problem of some spectroscopic measurements being constrained in some cases to a single laser stage where the beam pointing errors are sufficiently small to be tolerable. Then it has been necessary for users to realign and/or refocus the IR beam onto the region of tip-sample interaction before obtaining spectra in a wavelength range corresponding to a different laser stage. In the case that a quantum cascade laser is used as a radiation source it may be necessary to use several laser heads to cover a broad fraction of the mid-IR. Each of the laser heads may also have a slightly different emission angle making it very difficult to maintain the focus spot at the point of tip-surface interaction over a broad wavelength range. It is therefore desirable to enable a system to allow broadband spectroscopic measurements with sweeps of more than 500 $cm^{-1}$ and preferably more than 2000 $cm^{-1}$ without manual readjustment by the user.

BRIEF SUMMARY OF THE INVENTION

The Invention is applicable to an apparatus for producing an absorption spectrum in a localized region of a sample, using an Atomic Force Microscope, or other probe microscope capable of measuring probe-sample surface interactions on the micro and nanoscale. A beam of variable wavelength IR radiation, typically pulsed, is directed at the sample, and the AFM probe tip interacts with the sample. The response of the probe due to absorption of the IR radiation is measured. The apparatus includes at least one of a controllable beam steering mechanism and controllable beam focus mechanism.

In one embodiment, the invention is a method of measuring a response of the cantilever probe to at least one wavelength of the IR source and automatically adjusting the beam steering mechanism to substantially maximize the probe response. The adjusting step may be repeated at several wavelengths. In preferred embodiments, the beam steering mechanism sweeps the beam across a range of angles and determines an angle near the point of maximum probe response.

In various embodiments the beam steering mechanism adjusts the beam position in two axes. A map of the beam response may be determined and the adjustment point is selected to be the point on the map of substantially maximized response. For cases where the alignment variation from a previously measured wavelength is known to be small, a two dimensional crossing pattern may be employed in lieu of a full map. In preferred embodiments, the beam adjusting step is performed at a variety of source wavelengths and a table of adjustment positions vs wavelength is generated. This table is used to automatically adjust the beam position during acquisition of spectra. In a particular version of the invention, when a probe is exchanged in the force microscope, the beam steering mechanism is utilized to automatically align the beam to a region of the sample under the probe in less than five minutes and preferably less than one minute.

The invention also includes a method for using the beam focus mechanism to adjust the beam focus at least one source wavelength to substantially maximize probe response, preferably in conjunction with beam steering adjustment. In preferred embodiments, the beam focusing step is performed at a variety of source wavelengths and a table of focus settings vs wavelength is generated. This table is used to automatically adjust the beam focus during acquisition of spectra.

BRIEF DESCRIPTION OF THE DRAWINGS

The invention will be better understood by referring to the following figures.

DETAILED DESCRIPTION OF THE INVENTION

Figure 4:
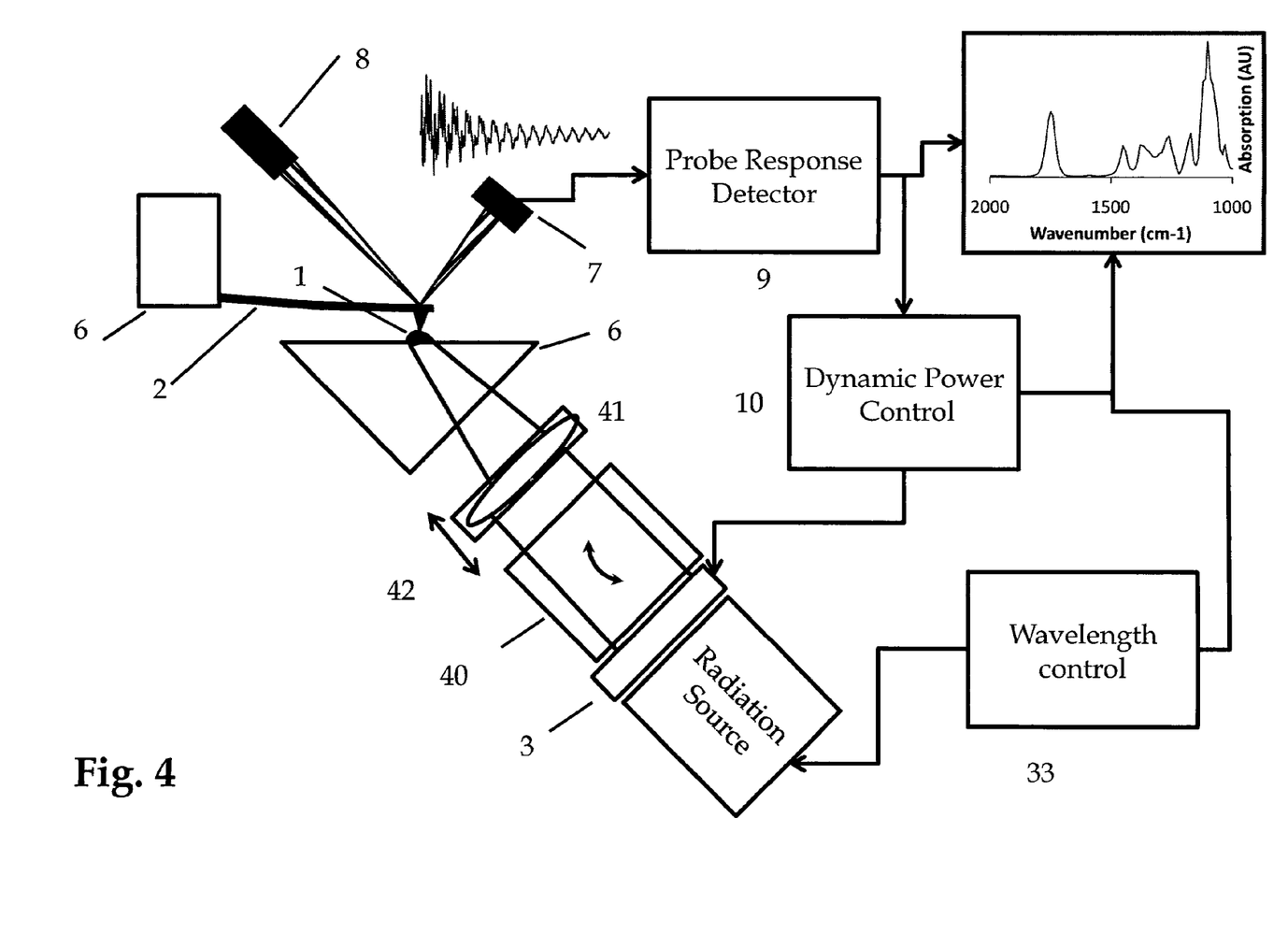
FIG. 4 is a block diagram of a PTIR system adapted to practice the invention

Referring to FIG. 4 the elements required to practice the invention are shown. Sample 1 is probed by an AFM with a cantilever probe 2. The interaction between the probe and sample may be contact, non-contact, near contact, intermittent contact and/or tapping or other method of interaction that generates a measurable probe response as a function of the interaction. In one embodiment an optical lever arm probe motion sensor comprising a source 8 and photodetector 7 interfaced to Probe Response Detector 9 measures a response of the AFM cantilever 2. The measured probe response may be deflection, motion, oscillation, phase or other properties of the mechanical response of the probe. Many techniques can be employed to measure the cantilever motion. For example AFMs have been built where the cantilever deflection is performed by electron tunneling, capacitive detection, interferometry, magnetic, piezoelectric, piezoresistive and thermal sensing, for example. Any mechanism that detects the cantilever deflection and/or motion may be sufficient. It is also possible to measure a probe response that is based on probe temperature and/or heat detected instead of or in addition to a probe displacement or motion. Relative motion is generated between the probe and sample by one or more scanning devices. Many different scanning devices can and have been applied in the art. It is understood that the AFM and the details of the scanning and probe detection methods are not part of the novelty of the invention and other AFM arrangements are possible.

To perform nanoscale infrared spectroscopy, a beam from a variable wavelength IR radiation source 3, is directed to a region of the sample. Mirrors, lenses and other optical components may be used to direct and focus the beam from the source onto a region of the sample.

Figure 3:
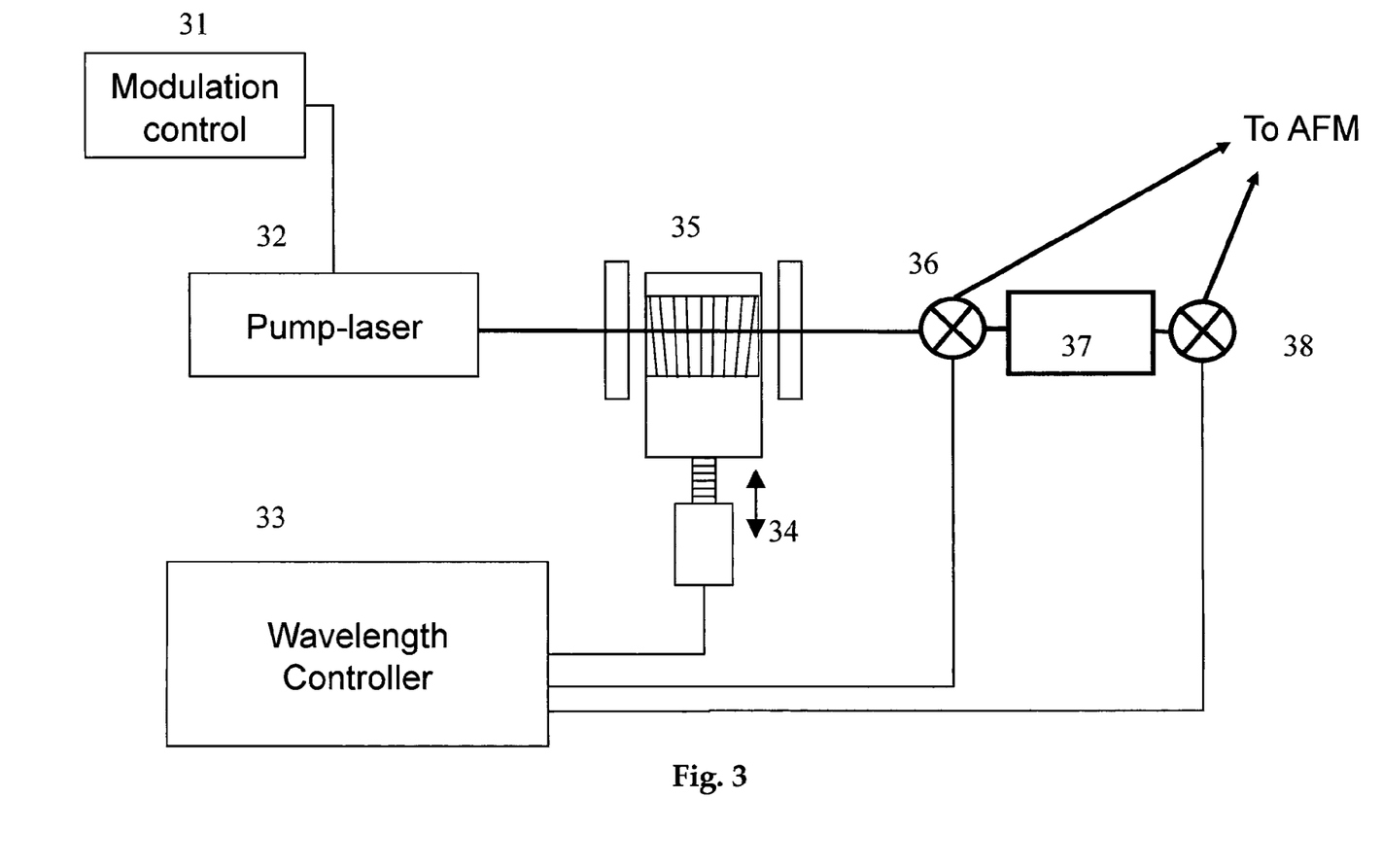
FIG. 3 is a simplified block diagram of an Optical Parametric Oscillator IR source

In one embodiment the source of radiation may be an optical parametric oscillator (OPO) that can be continuously tuned over a wavelength range from 2.5 microns to 10 microns, covering a major fraction of the mid-IR spectral range conventionally used in infrared vibrational spectroscopy. As shown in FIG. 3, a pump laser 32 is modulated 31 to produce suitable pulses these pulses are directed into a periodically poled crystal, for example periodically poled lithium niobate with fan shaped quasi phase matched grating periods 35 as shown. A wavelength controller 33 controls an actuator 34, which moves the fan across the beam. The pump laser beam generates photons at two different wavelengths (signal and idler) depending on the quasi phase match period at a given position, thereby shifting the Pump Laser beam in wavelength. Depending on the desired wavelength range, the beam may be directed directly to the AFM 36, or through a second stage 37 which can contain a second nonlinear optical crystal which generates even longer pulse wavelengths b, and then directed 38 to the AFM. Other sources of radiation may be employed, including visible or IR lasers, quantum cascade lasers, one or more quantum cascade lasers, a broadband source with a monochromator, a $CO_2$ laser, and/or a comb drive source. Any source that can provide an adjustable wavelength and sufficient power density to provide a measurable probe response may be used. Note that while the PTIR technique employs a pulsed radiation source, the problem of sample damage can also exist with CW sources and as such the dynamic power control schemes described herein are also applicable to CW sources.

In some tested versions of the system, the sample is mounted on a zinc selenide prism 6 in FIG. 4 and the illumination is performed by total internal reflection. Alternate approaches involve directing the beam to a region of the sample from above. Any means of directing a beam from the IR source to the sample, including the various means described in the referenced patent applications may be suitable. Wavelength is selected by wavelength control 33.

Dynamic power control 10 includes a variable attenuation capability and power control algorithms executing on one or more system controllers. The function of the dynamic power control is to adjust the optical power density delivered to the sample to keep the power density under a level where sample damage occurs. The power density can be controlled for example by changing the power of the beam and/or the focused beam size and/or the repetition rate of the pulsed laser.

In one embodiment the variable attenuator may be a wire grid polarizer, rotated under control of an electronic controller. Wire grid polarizers are available from several sources including Edmund Optics. Neglecting reflections and absorptions of the filter, amount of light transmitted through the polarizer varies like:

$$I = I_0 \cos^2 \theta \qquad \text{Eq. 1:}$$

where $I_0$ is the incident radiation and $\theta$ is the relative angle between source polarization and polarizer axis. Attenuation values between one and almost zero can be achieved by rotating the polarizer through ninety degrees. A specific attenuation value $I/I_0$ can be selected by choosing a polarizer angle:

$$\theta = \cos^{-1}\left(\sqrt{\frac{I}{I_0}}\right) \qquad \text{Eq. 2}$$

(In practice an offset angle parameter is usually required to adjust for mounting uncertainty in the polarizer and/or to select the optimal quadrant of the polarizer rotation.) Wire grid polarizers can be mounted conveniently on a hollow shaft motor, for example available from Nanotec. With a motor with 1.8 degrees per step and using a controller with 256 microsteps/step, 90 degrees of polarizer angle can be divided into 12,800 steps. For some applications it may be desirable to use other means for attenuation that can preserve beam polarization. Other means for variable attenuation in the IR spectrum include, an electronically controllable iris, a variable neutral density filter, direct control of the pump laser power current, or controller directed focusing optics to defocus the beam to reduce power at the sample. Motorized iris diaphragms for example are available from the Newport Corporation. Circular and linear variable neutral density filters are available from the Reynard Corporation. Laser pump current may be controlled by computer interface to a pump laser and/or by analog electronic control. Many motorized focus devices could also be employed to adjust the power density at the sample surface.

The dynamic power controller reads the probe response at a given source wavelength and dynamically adjust the variable attenuator if required. The power can be automatically adjusted prior to a spectral measurement or automatically at each wavelength and positional measurement point, or as often as needed based on the measured probe response. In this case "automatically" means that aside from initial set up of control parameters, the adjustment is performed without user intervention.

The probe response is dependent in part upon the IR absorption sample characteristics in the vicinity of the probe tip. Typically the probe sample interaction due to local absorption is in the form of a stimulated resonant oscillation of the cantilever and the measured response parameter is amplitude of the resonant signal. Alternatively, the probe may include a thermal sensor as known in the art, and the probe interaction may be temperature measurement either in addition to or possibly instead of resonant amplitude.

The dynamic power control capability allows for illumination power to be attenuated in areas of high absorption and/or at wavelengths where the source is more powerful, to reduce potential sample overheating which may distort the measurements. In areas of lower absorption or at wavelengths where less power is available, the attenuation can be reduced.

In a typical PTIR measurement cycle, the probe is placed at a region of the sample, and the source pulse illuminates the sampled at variety of center wavelengths covering some portion of the IR spectrum. The resonant oscillation is measured at each wavelength, from which an absorption spectrum may be generated. Then the probe may be moved to other regions of the sample and the spectrum procedure repeated, thus making an absorption spectrum map of the surface. In one mode, shown in FIG. 5, dynamic power control looks at the resonant probe amplitude at each wavelength and at each position, and adjusts the attenuation up or down depending on whether the amplitude is above a predetermined threshold indicating potential sample damage, or below a predetermined threshold to maintain adequate signal to-noise. Or data from the previous measurement may be used to adjust the current attenuation. Alternatively, the attenuation may be adjusted in feedback with the goal to keep the probe response (e.g. a resonant amplitude) at a set-point value. Note that in practice the probe response is not generally kept at a constant value by the feedback system. The reason is that at many wavelengths there is no significant absorption. In this case, the variable attenuator will open up to maximum power density, but the probe response may still remain below the setpoint value. This type of operation is perfectly acceptable and ensures that at any wavelength the signal-to-noise of the measurement is optimized at least up to the maximum available power from the radiation source.

The inventors have employed various strategies for calculating the desired attenuation value. In some cases, traditional PI or PID feedback has been employed. Alternately, simple ratiometric calculations have been applied using a two stage approach. For example the probe response can be averaged over a small number of IR source pulses (for example 8 pulses). This brief measurement can be compared to the target probe response to calculate an attenuator value for the actual data measurement. For example assume that an initial measurement of probe response gave a signal strength of $R_m$ using a starting attenuation value of $A_s$. In this case the next value of the attenuator setting $A_n$ will be given by:

$$A_n = A_s \frac{R_{sp}}{R_m} \quad \text{Eq. 3}$$

where $R_{sp}$ is the target setpoint value. In practice the values of $A_n$ are limited on the high and low end. At the high end, the attenuation is limited of course to a value of 1 (maximum power transmitted). The maximum attenuator value can also be capped at a lower value for a sensitive sample or near known strong absorption wavelengths. On the low end, the attenuation value can be limited to prevent the attenuation from going too close to zero which would cause additional noise during the normalization procedure described elsewhere. Note that since the IR source can be pulsed at kHz rates, the 8 pulses required to make a measurement for attenuation can have minimal impact on the spectral acquisition time.

For the case where the sample is mapped, data from previously measured points on the map close to the current point, like corresponding positions on adjacent scanlines or corresponding wavelengths from an adjacent point, may be used as look-ahead feedback to anticipate the attenuation values.

Figure 5:
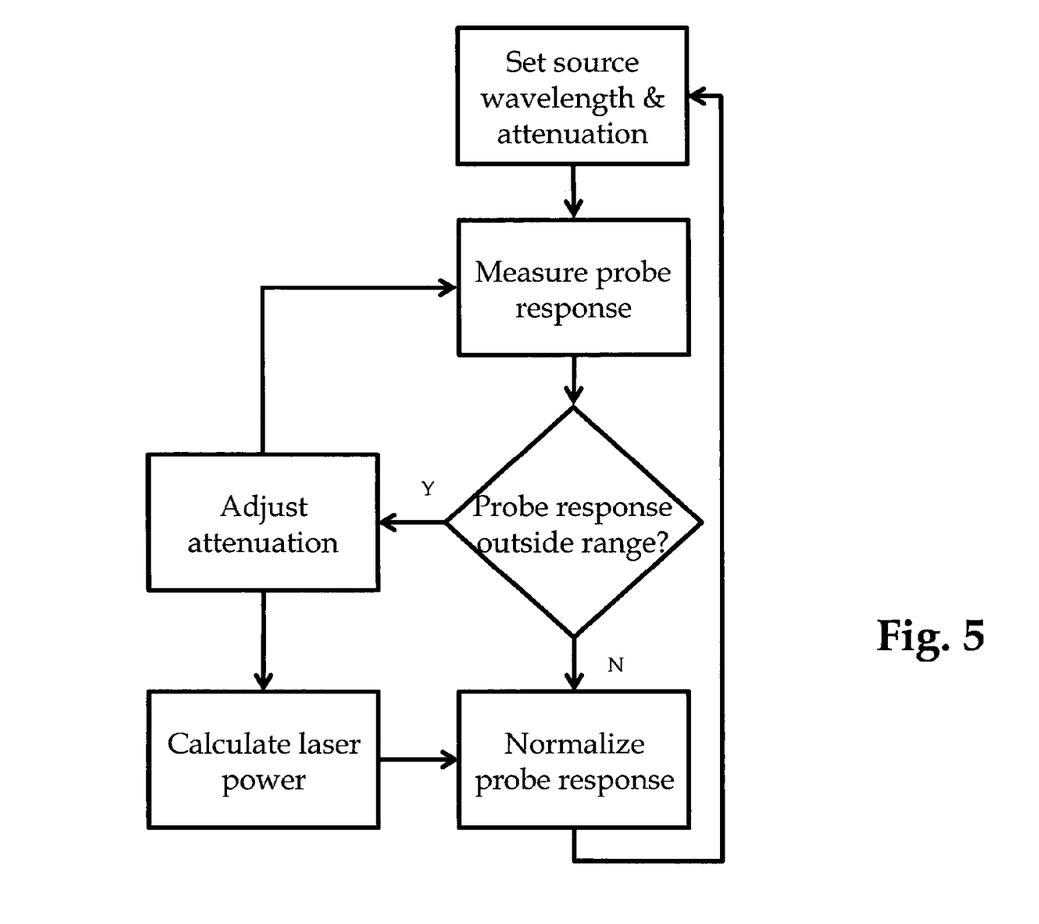
FIG. 5 is a flow chart of the method of the invention

One of the goals of this invention and the instruments described in the copending applications is to create a local IR absorption spectrum of a nanoscale region of a sample and have that spectrum have good correspondence to bulk spectra. This allows existing IR databases to be used to analyze and identify chemical components. To correlate well with IR spectral libraries, it is desirable to normalize the measured probe response by the radiation power density incident on the sample. Under the current invention, the power density incident on the sample is dependent both on the source output power as a function of wavelength and the attenuation value selected by either the user or automatically selected by the dynamic power controller. For example, a normalized absorption spectrum $I_{norm}(\lambda)$ can be created via an equation. An example of a straight forward normalization is:

$$I_{norm}(\lambda) = \frac{I(\lambda)}{P(\lambda)A(\lambda)} \quad \text{Eq. 4}$$

Where $I(\lambda)$ is the measured probe response, $P(\lambda)$ is the raw laser power and $A(\lambda)$ is the attenuation factor applied by the variable attenuator. Note that each of these factors may vary with radiation source wavelength $\lambda$. The radiation source power $P(\lambda)$ may be measured in advance or in real time as the spectra are acquired. In one embodiment, $A(\lambda)$ is the output of the dynamic power controller that is used to set the desired attenuation of the variable attenuator. In this way it is possible to infer the radiation power density incident on the sample (i.e. the two terms in the denominator of the equation above) by (1) measuring $P(\lambda)$ and (2) using the values of $A(\lambda)$ recorded during the spectrum. The values of $P(\lambda)$ may also be corrected for variations in power density associated with wavelength dependent focused spot size. The normalization step is shown in FIG. 5 as well.

Figure 6:
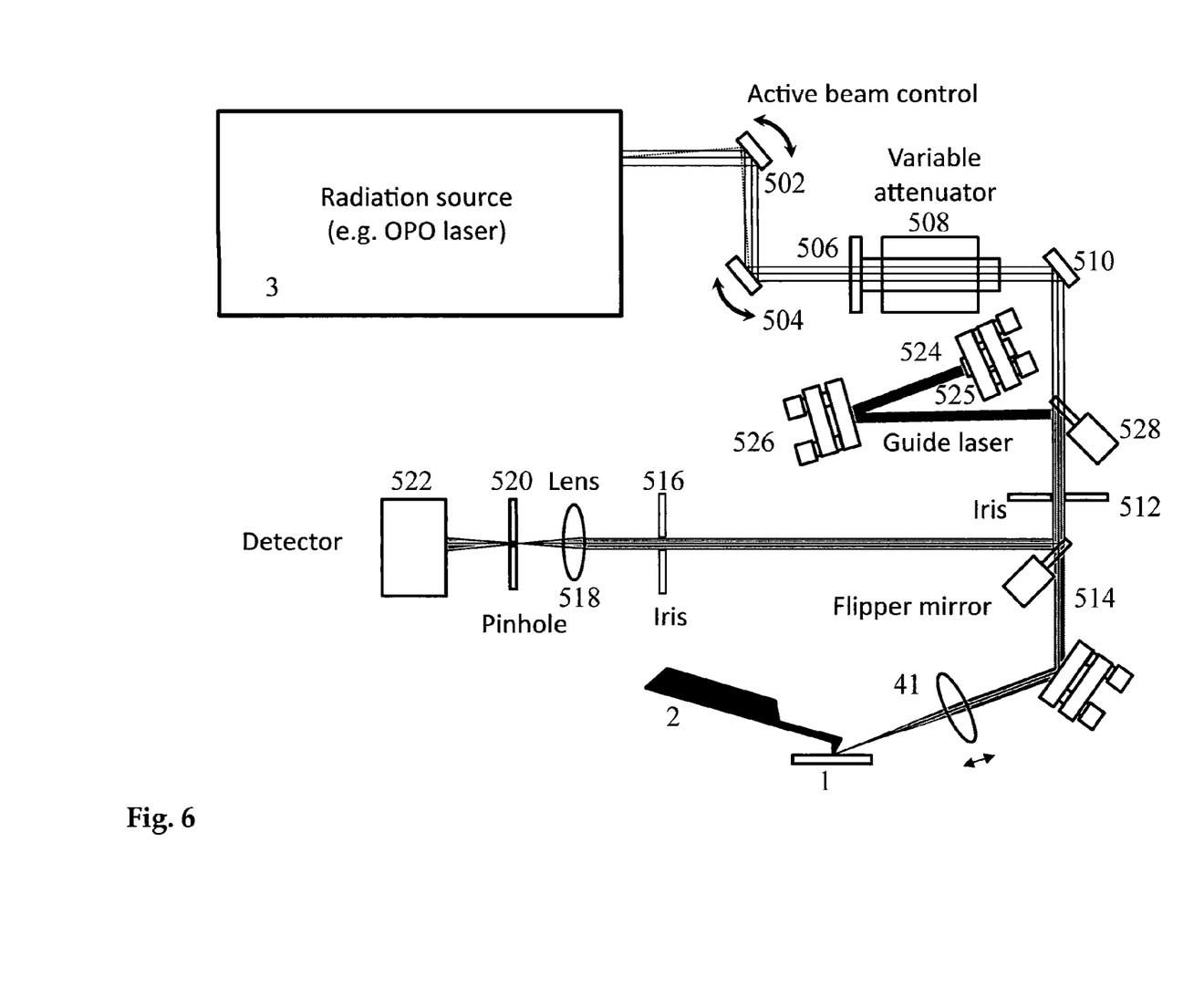
FIG. 6 is a simplified block diagram of instrumentation to provide dynamic beam angle control and radiation source power measurements

Because of the nature of some sources such as the OPO, the beam angle may vary as a function of wavelength, causing variation in the power actually delivered to the sample. Thus measuring total beam power at a power detector may not accurately represent the power at the sample. So in order to perform accurate measurements of $P(\lambda)$ and ensure alignment of the radiation beam with the cantilever probe, the inventors have developed a beam delivery system that integrates a reference path and dynamic beam positioning. As shown in FIGS. 4 and 6, the beam from radiation source 3 is directed towards a beam steering mechanism 40 that can comprise one or more electronically controlled mirrors 502 (FIG. 6) that perform active beam control. This mirror or mirrors can adjust the angle of the beam in one or two axes (one axis is shown for clarity). The electronically controlled mirrors can be adjusted using motorized actuators, piezoactuators or other actuators that tilt the mirror in at least one axis under electronic control. Other beam steering mechanisms that can deflect the beam angle and or beam center position under external control may also be suitable. Several companies including Newport sell motorized and piezo driven tip-tilt mirrors. Alternately, mirrors can be adjusted in a single axis by mounting the mirror to the shaft of a motor, for example a stepper motor or a DC servo motor. Two mirrors and motors can be combined to allow for two axis tip-tilt control. More motors and mirrors can be employed to allow for correction of beam angle and also beam offset. In one embodiment, the mirrors can be driven with a stepper motor and a motion controller that supports fine microstepping. For example, using a motor with 0.9 degrees per step and 256 microsteps per step, each microstep will provide 0.0035° of tilt adjustment of the mirror, or 0.007° of beam tilt. Using a 25 mm focal length lens to focus the IR beam to a spot, this gives positioning control of roughly 25 mm×tan(0.007°) or around 3 um laterally per step. Finer control can also be obtained using gearing, fine pitched screws with kinematic mirror mounts, and/or piezo driven mirror mounts. For applications requiring high speed tuning, it can be desirable to employ mirror control with high bandwidths. For example, an IR spectrum acquired in 100 msec may require as many as 1000 or more angle adjustments per second. Such beam control can be achieved for example with piezoelectric actuated tip-tilt stages. A number of companies also sell one and two axis galvonometer mirror scanners. It is also possible for the beam steering mechanism to employ other approaches to adjust the beam position, for example by translating a lens in the beam path such as the final focus lens 41, which is preferably automatically adjustable, used to create a focused spot in the region of the sample 1 under the probe tip 2. It is also possible to move the sample and probe to realign them to the beam as a function of wavelength. In the base of moving the final focus lens, probe and/or sample piezoelectric scanning mechanisms or similar devices can be used to achieve the desired translation relative to the incoming beam.

The beam steering mechanism is electronically controlled so that the beam position can be adjusted as a function of wavelength to correct for wavelength dependent beam pointing. This can be a significant issue in a broadly tunable laser system due to wavelength dependent refraction in the nonlinear optical crystals, for example, or other refractive elements in the beam path. The mirror(s) 502 may also be electronically adjusted to compensate for beam angle shifts with temperature or time. The beam steering mechanism should preferably be stable and repeatable in its positioning such that it can repeatably correct for wavelength dependent beam angle shifts. It can be desirable to employ position tracking mechanisms like initialization and step counting and/or optical encoding to maintain a stable reference position to ensure high accuracy in the beam position correction.

After leaving the active beam control mirror, the beam is directed via optional fixed mirror 504 to a variable attenuator. In one embodiment the variable attenuator is a wire grid polarizer 506 mounted on a hollow shaft motor 580. The beam is then directed by one or more mirrors 510 towards the probe 2 and sample 1. In the case that the radiation source provides an invisible beam (e.g. in the mid-IR), a visible guide laser can be used to mark the path of the IR beam. In this case, a guide laser 525 may be mounted in a tip-tilt stage 524 and the beam may then be directed to a second tip-tilt stage 526. These two tip-tilt stages provide sufficient degrees of adjustment to align the guide laser to be collinear with an IR beam from the radiation source. The collinearity adjustment can be performed by aligning both the guide beam and the IR beam through iris diaphragm's 512 and 520. Two flipper mirrors 514 and 528 can be employed to select the beam path. When flipper mirror 528 is down it blocks the IR beam and reflects the guide laser in its place. If the mirror is moved out of the beam path it allows the IR beam to pass to the AFM. Electronically controlled flipper mirrors are available from Newport and Thorlabs, for example. (Many alternate arrangements of mirrors and/or other electrical and optical components may be used to accomplish the same beam switching tasks).

An automatically adjustable focus lens 41 may be used to focus the beam from the IR source onto a region of the sample 1 under the cantilever probe tip 2. In one embodiment, focus lens 41 includes a motorized focus mount that can be moved to automatically optimize the probe response. Because of the variation of prism thickness with sample position and the wavelength dependence of the focus position, it has been advantageous to create an automatic focus algorithm that can automatically optimize the focus mechanism settings for different sample positions and different wavelengths. Although a focus optimization may be accomplished during acquisition of spectra, generally it is more convenient to calibrate for wavelength and sample thickness variations as a separate operation. In this mode, the system can store optimal focus positions for arbitrary sample positions and wavelengths and then rapidly go to these reference positions, even in the middle of a spectrum measurement to obtain optimal measurement sensitivity. Note that it is not always most desirable to focus the beam to achieve the smallest laser spot. While the smallest laser spot may achieve the highest beam energy density, a small spot also may require more precise control of the beam angle to maintain the beam adequately centered on the point of tip-sample interaction. In one embodiment, the IR beam is intentionally defocused to provide greater tolerance for misalignment. It should be understood that this implementation is within the scope of "substantially maximizing the probe response."

The second flipper mirror 514 may be used to direct a beam from the radiation source to a detector 522. This detector 522 may be used to measure the power as a function of wavelength for the normalization process described previously. A lens 518 and a pinhole 520 may also be used in front of the detector. If the pinhole 520 is placed at or near the focal point of lens 518 the detector can detect both shifts in radiation power and also shifts in beam angle. The reason is that if the incoming beam angle changes, the focal point will shift and a portion of the beam energy will be blocked by the pinhole. The active beam control mirror(s) 502 can be used to re-center the beam to maximize the power through the pinhole 520 and onto the detector 522. If flipper mirror 514 employs a beamsplitter element then this beam power measurement and active beam control can be performed dynamically during the process of acquiring spectra. It can also be performed as a calibration step and the optimal angles of mirror(s) 502 can be recorded for each wavelength. Using a detector with a lens and pinhole can be extremely useful for normalizing the probe response because this arrangement mimics the optical system used to excite the sample. When a beam from the IR source is focused on a region of the sample it generates a detectable signal when the focused spot of radiation overlaps with the area of probe-sample contact. If the angle of the beam changes due to wavelength or thermally induced shifts, the intensity focused in the region of the tip-sample contact will change as the focus spot centroid changes. The lens/pinhole/detector arrangement allows a reference measurement to be made that can detect and thus correct for changes in beam power intensity and beam angle.

It may be desirable to have some idea what thresholds for sample overheating are, beyond just looking for high response amplitudes. One possibility is to take measurements in one area of a sample, over a wide power range and determining limits before moving to second area for actual data taking measurements. One way to observe sample damage is to observe a rapid decrease in a contact resonant frequency as power is ramped up, due to sample softening when melting or other softening transition occurs. As discussed in the copending applications Ser. Nos. 11/803,421 and 12/315,859, when radiation is absorbed by a pulsed radiation source, the cantilever is shocked into oscillation. The frequencies of induced resonant oscillations correspond to vibration modes of the cantilever called contact resonances. The contact resonances are vibration modes that depend on both the mechanical properties of the sample and also the contact stiffness of the sample. If the sample undergoes a softening transition, the contact stiffness can change dramatically. When the contact stiffness drops, the contact resonant frequency also drops. Thus threshold radiation intensities can be determined by ensuring that the maximum beam power stays below a point where there is a significant change in a contact resonant frequency.

Figure 7:
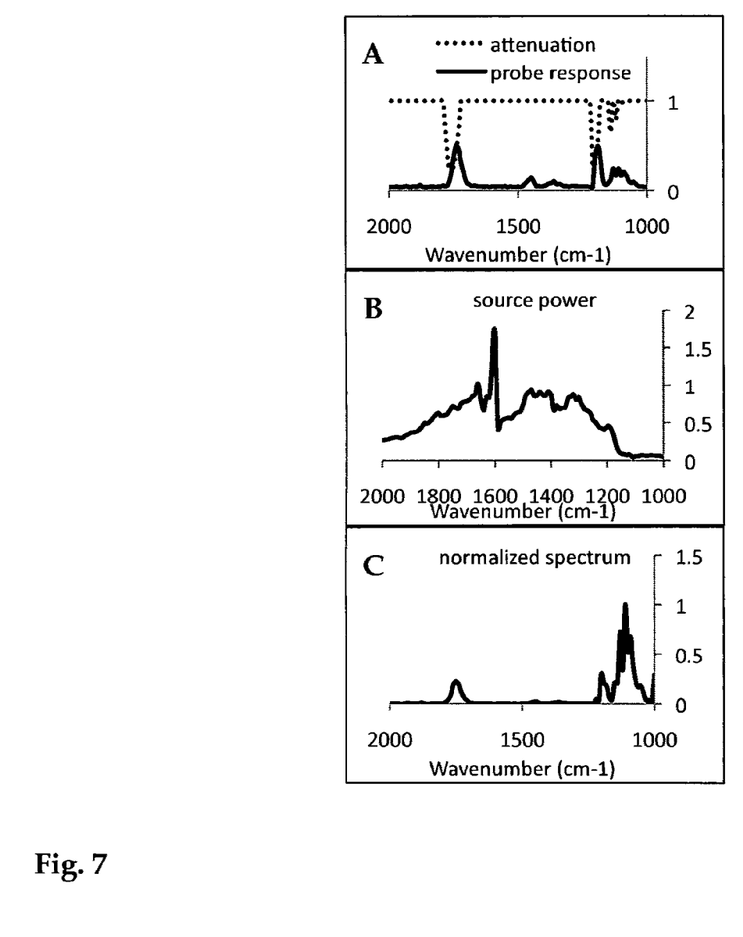
FIG. 7 shows sample spectral measurements employing the current invention with high dynamic range

FIG. 7 shows example measurements performed with one embodiment of the current invention employing dynamic power control and spectrum normalization. FIG. 7A shows the measured probe response under dynamic power control (solid line) and the attenuation value (dotted line) selected by the controller at each wavenumber (or equivalently, each wavelength). Note that the attenuator value dips at strong absorptions. As mentioned previously, this may keep incident radiation power below levels that can damage or alter the sample. FIG. 7B shows a measurement of radiation source power (in this case an OPO) as a function of wavenumber. The spectrum in FIG. 7C is normalized using the laser power curve in 7B along with the attenuation curve in 7A using the formula in equation 4. The dynamic range in this example measurement is around 2300, obtained by comparing the peak amplitude at around $1110 \, cm^{-1}$ versus the average baseline noise level between $1800$-$2000 \, cm^{-1}$. By comparison on some materials, the dynamic range without dynamic power control of the current invention can be on the order of ten. For example, the raw probe response in FIG. 7A has a dynamic range of only around 12. Without dynamic power control it would have been necessary to select a laser power such that the sample was not damaged at the highest absorption peak, thus leading to significantly lower signal to noise. For example, the signal to noise ratio in the normalized spectrum in FIG. 7C is around 400.

Figure 8:
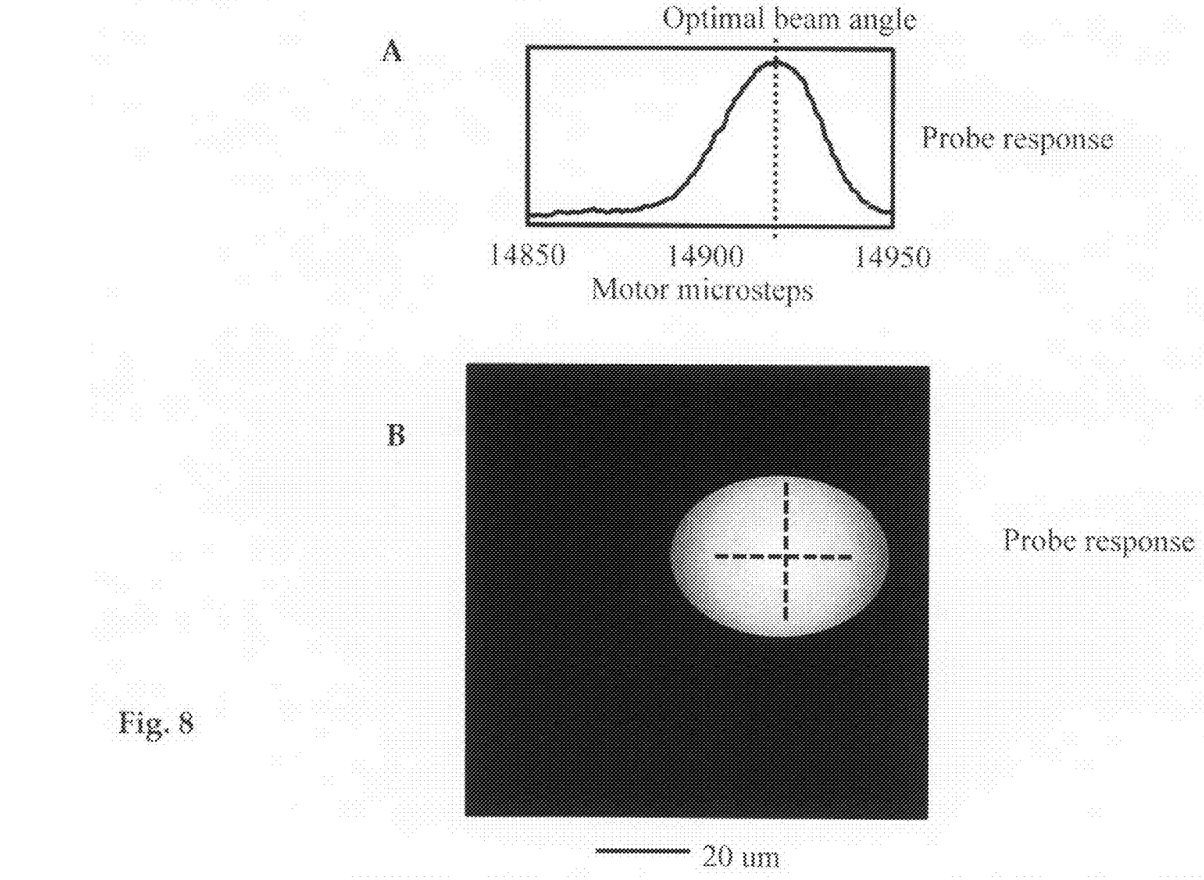
FIG. 8 depicts the 1 and 2 dimensional response of the probe as a function of beam steering position.

Returning to FIG. 6, it is also possible to use the beam steering mechanism to automatically align and optimize the position of the IR beam on the sample 1 under the tip of the cantilever probe 2. Such optimization can be performed without user intervention. There are several ways this can be accomplished. First, the beam steering mechanism can be swept in a single axis to locate the beam position (or equivalently mirror angle) of maximum probe response to radiation absorbed by the sample. An example of a probe response to a single axis sweep is shown in FIG. 8A. Such sweeps can be performed sequentially and/or iteratively between multiple axes of angle adjustment. It is also possible to employ more elaborate search algorithms. In one embodiment it is possible to sweep the beam steering mechanism in two substantially orthogonal axes while measuring the probe response at a plurality of beam positions. From these data it is possible to construct a map of probe response versus beam position (or mirror angle) in two beam axes. The optimal beam position (or angles) for the beam steering optics may be determined from beam position where probe response is substantially maximized, for example. An example measurement is shown in FIG. 8A where the angle of a motorized mirror mount was adjusted while the amplitude of the induced cantilever oscillation was measured. From this type of measurement it is possible to determine the optimal beam position with an uncertainty of less than a few microns. It is thus possible to apply a correction at each selected wavelength that ensures that the beam is position with its center substantially aligned with the point of tip-sample interaction. Such alignment is performed with an accuracy of better than 30 microns and preferably better than 5 microns. For better reliability it may also be preferable to calculate the centroid angles from the distribution of probe response versus beam position or angle. It may also be desirable to fit a curve, for example a gaussian to the measured data to determine the optimal position/angles for the beam steering mechanism.

It is also possible to employ any of a variety of efficient search algorithms to choose a subset of beam steering angles to locate the maximum probe response without performing a complete 2D raster scan required to make a full map. For example gradient ascent techniques can be used to find an efficient trajectory to the maximum probe response. Additionally, recursive variable resolution search algorithms can be employed. For example, it is possible to start out with the final focus lens intentionally defocused to create a large focus spot, for example more than 100 um in diameter. This allows the search routine to begin with coarse spatial resolution, on the scale of 100 um per pixel such that a raster scan or other sweep can be completely quickly with only a few measurement points required. Once a coarse alignment position is obtained, the spatial resolution of the alignment sweep can be increased, centered on the maximum found in the coarse sweep, the focus position can be refined resulting in a smaller focus spot. The dynamic power control capabilities also provide a significant benefit during the beam alignment procedure as it allows for the power to be turned up when the beam focus spot is large and turned down as the beam spot is made successively smaller. For a case where the beam is already substantially aligned, such as when a relatively small wavelength change is made, even simpler and faster approaches may be used, for example using a spiral search pattern starting at the expected beam center position.

FIG. 8B shows a two-dimensional map of probe response vs beam position on the sample. If a small wavelength change is made, it is known that the beam position change will be relatively small as well. For such a case or other situations where the position is at least partially known, a simple cross sweep such as depicted in the figure, may be sufficient to determine optimal beam alignment.

The automated maximization process can prove extremely useful, especially when it is necessary to change the cantilever probe tip and/or sample. When manually changing a probe tip, for example, the position of the apex of the probe may vary by many tens or even hundreds of microns from previous position. Thus, it is likely the new probe will not be at the maximum energy point of the IR beam based on a previous alignment step. In current PTIR systems it is necessary for the user to manually seek out and align the invisible IR beam upon installing each new cantilever probe. This can be a time consuming process, requiring 10 minutes to an hour or more, even for experienced users. Using the beam steering mechanism to automatically sweep over a plurality of beam angle positions, and an algorithm to determine angles corresponding to the maximum probe response, this alignment procedure can be completed automatically and without user intervention in timescales of less than 5 minutes or even less than 1 minute. However it may still be useful to use the visible alignment beam to roughly position the IR beam, so retaining the visible alignment tool is desirable.

In addition to speed advantages, the automated beam alignment algorithm also can improve the quality of the spectra obtained by the measurement apparatus. It has been observed that small changes in the alignment of the IR laser can dramatically affect the frequency content of the cantilever ringdowns resulting from absorption of IR pulses by the sample. It has also been observed, that some of the resonant peaks are more sensitive to background forces that are not local to the apex of the probe tip. This was discussed in co-pending application Ser. No. 12/315,859 which is incorporated by reference (see for example FIG. 17 and associated text of the co-pending application). Because of this, it may be desirable to optimize the alignment of the IR beam based on maximizing the probe response at a specific resonance mode, rather than the overall peak-to-peak response. Optimizing the amplitude of a single mode, for example the second mode of cantilever oscillation, may result in improved signal-to-background and/or improved spatial resolution.

As discussed above for automated wavelength-dependent focus adjustment, it may be convenient to calibrate beam alignment wavelength dependence separately from actual spectra acquisition. Using some combination of the techniques disclosed above, optimal beam alignment at multiple wavelengths covering a spectral range of interest may be determined and stored, for example in a look-up table. Then during actual spectral data acquisition, the beam position may be quickly adjusted at each wavelength.

It should be noted that an automated probe alignment algorithm, as is known in the art, may also be combined with wavelength dependent beam angle corrections. A table of optimal beam angles versus wavelength can be created using the reference detector 522. Then the optimal angle for directing the beam to the probe tip can be determined by sweeping the beam steering mechanism to substantially maximize the probe response at one or more wavelengths. An angular offset can be then calculated to determine the required beam shift between the reference detector and the probe. Note that the functions of flipper mirrors 514 and 528 and the functions of electronically controlled mirrors 522 can be combined into the same mechanism. Specifically it is possible to use two mirrors mounted on rotary motor shafts and arranged with the motor shafts orthogonal to each other. In this case, the flipper motor functions can be achieved by rotating the mirrors by a substantial amount, for example 90 degrees, where the beam steering can be accomplished using motion of a small number of fine motor steps.

It will be apparent to the skilled artisan that there are numerous changes that may be made in embodiments described herein without departing from the spirit and scope of the invention. Other features not mentioned in the specification, but known to one skilled in the art may be integrated as well without departing from the spirit and scope of the present invention. There is, for example, a wide array of materials, apparatuses, and methods which may be interchangeably used, and there are many changes that may be made in dimensions and so forth to accommodate different needs which may be used, all within the scope of the invention. The methods, system, and apparatuses of the present invention should therefore be afforded the broadest possible scope under examination. As such, the invention taught herein by specific examples is limited only by the scope of the claims that follow.

We claim:

1. A method of obtaining wavelength dependent optical property measurements of a sample, with a probe microscope and an IR radiation source tunable over a range of wavelengths, the method comprising:
   a) interacting a probe of the probe microscope with a region of the sample;
   b) adjusting a position of a beam of radiation emitted from the radiation source with a beam steering mechanism;
   c) directing a beam from the radiation source and beam steering mechanism at the region of a sample under the probe;
   d) measuring a response of the probe due to an interaction of radiation with the sample at at least one wavelength of radiation;
   e) automatically adjusting the beam steering mechanism to substantially maximize the measured probe response.

2. The method of claim 1 wherein the beam adjusting step is repeated for a plurality of beam wavelengths to create an absorption spectrum of a sub-micron region of the sample.

3. The method of claim 2, further comprising the step of building a table of optimal beam angles as a function of wavelength wherein the optimal beam angles correspond to angles where the probe response is substantially maximized.

4. The method of claim 3, wherein the table of optimal beam angles is used to correct for wavelength dependent pointing variation in the tunable source of radiation.

5. The method of claim 2 wherein a spectrum of a region of a sample is created by measuring probe response over a wavenumber range of at least 500 cm−1.

6. The method of claim 2 further comprising the step of focusing the beam from the IR source and beam steering mechanism to a focused spot and wherein the automatic adjusting step maintains the position of the focus spot substantially centered on a point of probe-sample interaction with an accuracy of better than 30 microns in at least one axis.

7. The method of claim 6 where the automatic adjusting step maintains the position of the focus spot substantially centered on a point of probe-sample interaction with an accuracy of better than 5 microns in at least one axis.

8. The method of claim 1 wherein the beam steering mechanism adjusts the beam position by adjusting angles of the beam in two axes.

9. The method of claim 8 wherein the adjusting step includes creating a two dimensional map of probe response versus beam angle in the two substantially orthogonal directions.

10. The method of claim 9 further comprising the step of selecting a final adjustment point of the beam steering mechanism based on identifying a point on the two dimensional map corresponding to a point of substantially maximum probe response on the map.

11. The method of claim 1 wherein the adjusting step substantially maximizes the measured probe response by sweeping the beam steering mechanism across a range of adjustment positions and selecting a position substantially near the point of maximum probe response.

12. The method of claim 1 wherein the wavelength dependent optical property comprises an absorption spectrum of a region of a sample.

13. The method of claim 1 further comprising the step of:
   a) adjusting a focal point of the beam of radiation emitted from the radiation source with an adjustable beam focus mechanism; and
   b) adjusting the focus mechanism to substantially maximize the measured probe response at at least one wavelength of beam radiation.

14. The method of claim 13 further comprising the step of recursively adjusting the beam steering mechanism and the beam focus mechanism to substantially maximize the measured probe response.

15. The method of claim 14 further comprising the steps:
   a) adjusting a focal point of a beam of radiation emitted from the radiation source with an adjustable beam focus mechanism;
   b) automatically adjusting the focus mechanism to substantially maximize a measured probe response.

16. The method of claim 15 further comprising the steps:
   a) adjusting power of the beam of radiation with a variable attenuator;
   b) recursively adjusting the beam steering mechanism, the variable attenuator, and the focus mechanism to substantially align the beam to the probe.

17. A method of obtaining wavelength dependent optical property measurements of a sample with a probe microscope and an IR radiation source tunable over a range of wavelengths, the method comprising:

a) interacting a probe of the probe microscope with a region of the sample;
b) adjusting the focus of a beam of radiation emitted from the IR radiation source with a beam focusing mechanism;
c) directing a beam from the radiation source and beam focusing mechanism at the region of a sample under the probe;
d) measuring a response of the probe due to an absorption of radiation by the sample at at least one wavelength of radiation;
e) automatically adjusting the beam focusing mechanism to substantially maximize the amplitude of measured probe response at the at least one wavelength.

18. The method of claim 17 wherein the beam focusing step is repeated for a plurality of beam wavelengths.

19. The method of claim 18, further comprising the step of building a table of optimal beam focus settings as a function of wavelength wherein the optimal beam focus correspond to settings where the probe response is substantially maximized.

20. The method of claim 19, wherein the table of optimal beam focus settings is used to correct for wavelength dependent focusing variation in the tunable source of IR radiation.

21. A method obtaining wavelength dependent optical property measurements of a sample using a probe microscope and a source of IR radiation tunable over a range of wavelengths, the method comprising:
a) exchanging a probe in the probe microscope;
b) adjusting a position of a beam of radiation emitted from the radiation source with a beam steering mechanism;
d) directing a beam from the beam steering mechanism at a region of a sample;
e) automatically aligning the beam to the probe in a total time of less than 10 minutes;
f) interacting the probe with a region of the sample;
g) measuring a probe response as a function of wavelength of the IR source.

22. The method of claim 21 wherein the automatic aligning step is performed by substantially maximizing the probe response.

23. The method of claim 21 wherein the aligning step (f) is accomplished in less than 1 minute.

* * * * *